United States Patent [19]

Traver et al.

[11] Patent Number: 5,240,698
[45] Date of Patent: Aug. 31, 1993

[54] AMINOFUNCTIONAL SILICONE COMPOSITIONS AND METHODS OF USE

[75] Inventors: Frank J. Traver, Troy; Bianca K. Thayer, Greenwich, both of N.Y.

[73] Assignee: General Electric Co., Waterford, N.Y.

[21] Appl. No.: 851,416

[22] Filed: Mar. 13, 1992

Related U.S. Application Data

[62] Division of Ser. No. 591,908, Oct. 2, 1990, Pat. No. 5,132,443.

[51] Int. Cl.$^5$ ............................ A61K 7/09; A61K 7/11
[52] U.S. Cl. ........................................ 424/71; 424/70; 427/384; 427/387; 8/115.7; 8/181; 8/127.51; 8/129; 8/115.64; 252/106; 252/107; 252/117
[58] Field of Search .................... 424/70, 71; 427/387, 427/384; 8/115.7, 181, 127.51, 129, 115.64; 252/106, 107, 117

[56] References Cited

U.S. PATENT DOCUMENTS

| | | | |
|---|---|---|---|
| 2,921,950 | 1/1960 | Jex et al. | 260/448.2 |
| 3,033,815 | 5/1962 | Pike et al. | 260/46.5 |
| 3,890,269 | 6/1975 | Martin | 260/46.5 |
| 4,247,592 | 1/1981 | Kalinowski | 428/266 |
| 4,559,227 | 12/1985 | Chandra et al. | 424/70 |
| 4,563,347 | 1/1986 | Starch | 424/70 |
| 4,601,902 | 7/1986 | Fridd et al. | 424/70 |
| 4,661,577 | 4/1987 | Lane et al. | 528/10 |
| 4,902,499 | 2/1990 | Bolish et al. | 424/74 X |
| 4,915,938 | 4/1990 | Zawadzki | 424/71 X |
| 5,063,044 | 11/1991 | Kohl et al. | 424/71 X |
| 5,066,481 | 11/1991 | Helioff et al. | 424/71 X |
| 5,089,253 | 2/1992 | Halloran | 424/71 X |
| 5,108,738 | 4/1992 | Halloran et al. | 424/71 X |
| 5,120,532 | 6/1992 | Wells et al. | 424/71 X |
| 5,126,126 | 6/1992 | Varaprath et al. | 424/71 |

FOREIGN PATENT DOCUMENTS

| | | |
|---|---|---|
| 0180464 | 5/1986 | European Pat. Off. |
| 0240350 | 10/1987 | European Pat. Off. |
| 1153488 | 8/1963 | Netherlands |
| 1175120 | 12/1969 | United Kingdom |

OTHER PUBLICATIONS

Makromolekulare Chemie, Macromolecular Symposia. vol. 6, No. 6, Dec. 1986, Basel CH pp. 67–80.
J. E. McGrath et al.: 'Kinetics, Mechanisms, and Systhesis Studies of Difunctional Aminopropyl Terminated Polydimethylsiloxane Oligomers' 1986 pp. 67–71.
Disapio, A. & Fridd, P. Silicones: Use of Substantive Properties On Skin and Hair, International Journal of Cosmetic Science 10, 75–89 (1988)–to be furnished.

*Primary Examiner*—Paul F. Shaver

[57] ABSTRACT

There are provided novel diorganoaminoorganosiloxyterminated polysiloxanes and compositions thereof which provide improved properties to hair and textile fabric treated with them. Methods for treating hair and fabric with the polysiloxanes and compositions containing them are also provided.

24 Claims, No Drawings

AMINOFUNCTIONAL SILICONE COMPOSITIONS AND METHODS OF USE

This application is a division, of application Ser. No. 07/591,908, filed Oct. 2, 1990, now U.S. Pat. No. 5,132,663.

BACKGROUND OF THE INVENTION

The present invention relates to aminofunctional silicone compositions. More particularly, this invention relates to novel aminofunctional silicone compositions and their use as hair-treating and fabric-treating agents.

It is well known in the art that organopolysiloxanes give hair glossiness, suppleness, smoothness, and softness. The use of aminoalkyl substituted polydiorganosiloxanes in hair care compositions is also well known. Reference is made, for example, to Disapio, A. and Fridd, P., Silicones: Use of Substantive Properties On Skin and Hair, *International Journal of Cosmetic Science* 10, 75-89 (1988); and U.S. Pat. Nos. 4,563,347 (Starch), 4,601,902 (Fridd et al.), and 4,749,732 (Kohl et al.).

For example, Disapio, A. and Fridd, P., Silicones: Use of Substantive Properties On Skin and Hair, *International Journal of Cosmetic Science* 10, 75-89 (1988) disclose the use of two types of aminofunctional silicones, i.e., amodimethicone and trimethylsilylamodimethicone, as hair treating agents.

U.S. Pat. No. 4,563,347 to Starch discloses a hair conditioning composition containing a siloxane having the general formula

wherein R is a functional group which provides attachment to the hair, X is hydrogen, phenyl, hydroxyl, and saturated hydrocarbon radicals, a has a value of 0-3, b has a value of 0-1, and n+m has a value of 1 to 2000. The functional groups represented by R have the formula $C_yH_{2y}Z$ wherein y has a value of 2 to 8 and Z can be, among other things, $-NH_2$. The functional groups are located on the terminal units of the siloxane and along the chain. The siloxane in Starch does not appear to contain trifunctional siloxy units, but only monofunctional and difunctional units.

U.S. Pat. No. 4,601,902 to Fridd et al. (Fridd) discloses the use in a hair treating composition of a polydiorganosiloxane having in the molecule at least one group represented by the general formula $=SiR^{11}NHR^{111}$, wherein $R^{11}$ is an alkylene group and $R^{111}$ is hydrogen, an alkyl group, or an aliphatic hydrocarbon group attached to the nitrogen atom through a carbon to nitrogen bond and containing at least one group selected from $-NH-$ and $-NHZ-$ groups wherein Z is hydrogen or an alkyl group. The location of the $=SiR^{11}NHR^{111}$ group is not specified in Fridd.

U.S. Pat. No. 4,749,732 to Kohl et al. (Kohl) discloses a hair care composition containing an organopolysiloxane having attached along its chain silicon-bonded units of the formula $-R^1NQ[(CH_2)_bNQ]_pCHR^2CHR^3COOR^4$ wherein $R^1$ is an alkylene radical, $R^2$ is hydrogen, phenyl, or alkyl radical, $R^3$ is hydrogen or methyl, $R^4$ is an alkyl radical, p has a value of 0, 1, or 2, b has a value of 2, 3, or 4, and Q is hydrogen, an alkyl radical, or a $-CHR^2CHR^3COOR^4$ radical.

U.S. Pat. No. 4,559,227 (Chandra et al.) discloses a conditioning shampoo containing an amine functional siloxane polymer of the formula:

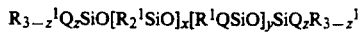

wherein $R^1$ is an alkyl or a phenyl group, Q is an amine functional substituent of the formula $-R^{11}Z$, wherein $R^{11}$ can be a divalent alkylene radical and Z can be $-NH_2$, z has a value of 0 or 1, x has an average value of 25 to 1000, y has an average value of 0 to 100 when z is 1, and y has an average value of 1 to 100 when z is 0.

The use of aminofunctional polysiloxanes as sizing agents for textile fabric materials is also known in the art. Reference is made, for example, to U.S. Pat. Nos. 2,921,950 (Jex et al.), 3,033,815 (Pike et al.), 3,890,269 (Martin), 4,661,577 (Jo Lane et al.), and 4,247,592 (Kalinowski).

U.S. Pat. No. 2,921,950 (Jex et al.) discloses aminofunctional organopolysiloxanes useful as sizes for fibrous glass materials and containing units of the formula $[H_2NCH_2CH_2SiO_{1.5}]$ and the formula $[R^{111}{}_nSiO_{4-n/2}]$, where $R^{111}$ is an alkyl group or an aryl group, and n has an average value of from 1 to 3 inclusive.

U.S. Pat. No. 3,033,815 (Pike et al.) discloses copolymeric aminoalkylpolysiloxanes containing the structural units:

wherein R is an alkyl group, a is an integer having a value of at least 3, b is an integer having a value of from 0 to 2, $R^1$ is an alkyl or aryl group, and e is an integer having a value of from 0 to 2.

U.S. Pat. No. 3,890,269 (Martin) is directed to a method for making aminofunctional organopolysiloxanes by reacting in the presence of a catalyst an organopolysiloxane and an aminofunctional silane or siloxane which may have the formula

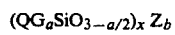

wherein Q can represent $H_2NR^{111}$, wherein $R^{111}$ can be divalent hydrocarbon radical, G can represent a monovalent hydrocarbon radical, a is a number of from 0 to 2, x is a number of from 1 to 20,000, Z is a radical selected from the group consisting of $R^{11}O_{0.5}$, $R_3SiO_{0.5}$ and $R^{11}{}_2NR^{111}O_{0.5}$, wherein $R^{11}$ is hydrogen or a monovalent hydrocarbon radical, and $R^{111}$ is as defined above.

U.S. Pat. No. 4,247,592 (Kalinowski) discloses the treatment of synthetic fibers with a composition containing a triorganosiloxane-endblocked polydiorganosiloxane consisting essentially of terminal triorganosiloxane units of the formula $R_3SiO_{\frac{1}{2}}$ and backbone diorganosiloxane units of the formula $R_2SiO_{2/2}$, wherein R is either a nitrogen-containing radical of the formula $-R^1(NHCH_2CH_2)_aNHR^1$ or a methyl radical. $R^1$ is a lower alkylene radical and $R^{11}$ is hydrogen or a lower alkyl radical, and a is 0 or 1. The triorganosiloxane-endblocked polydiorganosiloxane contains approximately two silicon-bonded amino radicals of the formula $-R^1(NHCH_2CH_2)_aNHR^{11}$.

U.S. Pat. No. 4,661,577 (Jo Lane et al.) discloses aminofunctional polysiloxanes used for treating fabrics, wherein the polysiloxane is substantially trialkylsiloxy terminated and has at least one amino or substituted amino group linked to at least one trifunctional siloxy unit of the polysiloxane through an alkylene or arylene bridge.

The amodimethicones, which are frequently used as hair-treating and fabric-treating agents, are silanol-stopped and undergo condensation cure to form Si—O—Si units. However, the curable nature of these polymers leads to certain drawbacks in their use in hair treating or fabric treating compositions, such as buildup, making the compositions difficult to remove.

It is desirable, therefore, to provide hair-treating and fabric-treating compositions containing non-curable aminofunctional silicones.

The known hair-treating or fabric-treating compositions containing non-curable aminofunctional silicone compositions generally provide good conditioning properties. However, it is continually desirable to provide other non-curable aminofunctional silicone compositions which provide comparable or improved conditioning characteristics to hair and good hand qualities to fabric.

Thus, it is a primary object of the present invention to provide novel non-curable aminofunctional silicone compositions which impart good conditioning properties to hair and good hand properties to fabric.

Another disadvantage to the use of amodimethicone and trimethylsilylamodimethicone polymers in hair-treating or fabric-treating compositions is the presence in these polymers of secondary amines. Secondary amines tend to become yellow during oxidation.

It is therefore a further object of this invention to provide an aminofunctional silicone for use in hair-treatment or fabric-treatment compositions wherein the silicone does not contain secondary amines.

These objects and others are achieved in the present invention.

In general, the performance of an aminofunctional silicone containing amine-substituted hydrocarbon groups bonded to silicon atoms along the polysiloxane chain as opposed to the terminal silicon atoms has been found to depend on the level of amine equivalence, structure (i.e., linear versus branched), and viscosity. Better conditioning properties are provided by aminofunctional polysiloxanes having higher levels of amine equivalence, a linear rather than a branched structure, or higher viscosity.

The present invention is based on the discovery that properties comparable to or somewhat better than those of high viscosity, linear polysiloxane containing high levels of amine equivalence can be achieved with a low viscosity, branched polysiloxane having relatively low levels of amine equivalence.

SUMMARY OF THE INVENTION

Accordingly, one aspect of the present invention is directed to a diorganoaminoorganosiloxy-terminated polysiloxane having the general formula:

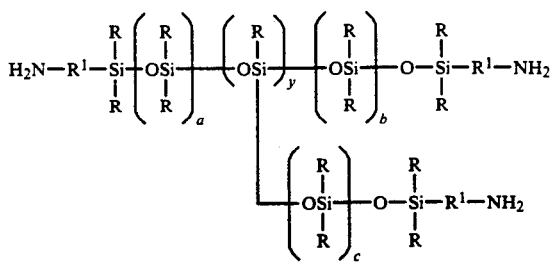

wherein each R is independently a substituted or unsubstituted hydrocarbon radical; each $R^1$ is independently a divalent alkylene, alkarylene or arylene radical; a, b, and c are numbers having values such that the sum $a+b+c$ equals a number ranging from about 20 to about 1000; each y is a number ranging from about 1 to about 100; the amine equivalent of the polysiloxane ranges from about 0.05 to about 2.0; and the viscosity ranges from about 20 to about 5000 centipoise at 25° C.

Another aspect of the present invention is directed to a composition, comprising:

(A) from about 0.1% to about 5.0% by weight of the diorganoaminoorganosiloxy-terminated polysiloxane having the general formula set forth above; and (B) from about 95% to about 99.9% by weight of a diluent selected from the group consisting of a physiologically acceptable organic solvent and an aqueous emulsion comprising water and an effective amount of an oil-in-water type surfactant.

The composition set forth above is useful as a hair treating or as a fabric treating composition.

This invention is also directed to a method of conditioning hair which comprises the step of contacting hair with an effective amount of the composition described above.

This invention is further directed to a method of treating textile fabric which comprises the step of contacting the textile fabric with an effective amount of the composition described above.

The composition of this invention imparts improved or comparable wet and dry combing, softness and flexibility properties to hair, while causing less irritation to the skin and providing sheen and gloss characteristics comparable to those of aminofunctional silicone conditioning agents presently in use.

DETAILED DESCRIPTION OF THE INVENTION

The novel aminodialkysiloxy-terminated polydiorganosiloxanes of the present invention are useful in such hair treating compositions as conditioners, rinses, shampoos, aerosols, pump sprays, lotions, creams or mousse-type compositions.

The term "hair" as used in the present invention includes treated and untreated human hair, animal hair, and any type of fiber that needs gloss, reduced fly-away and ease of combing. Treated hair includes hair that is chemically changed and/or damaged by permanents and dyes.

Textile fabrics suitable for use in this invention include, for example, polyester, polyester cotton, polyester cotton, polyester rayon, cotton, rayon, nylon, and the like.

The novel aminofunctional silicones of the present invention are represented by the general formula:

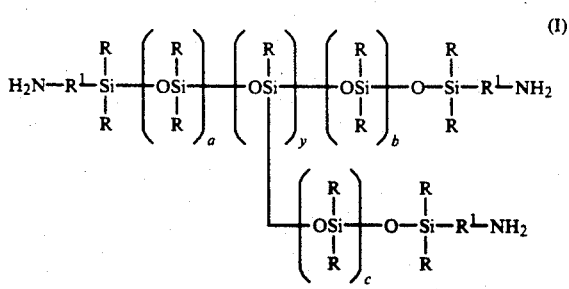

wherein each R is independently a substituted or unsubstituted hydrocarbon radical; each $R^1$ is independently a divalent alkylene, alkarylene or arylene radical; a, b, and c are numbers having values such that the sum a+b+c equals a number ranging from ranging from about 20 to about 1000; each y is a number ranging from about 1 to about 100; the amine equivalent of the polysiloxane ranges from about 0.05 to about 2.0; and the viscosity ranges from about 20 to about 5000 centipoise at 25° C.

Examples of groups represented by R in Formula (I) above include alkyl radicals; aryl radicals; alkenyl radicals; alkaryl radicals; and radicals wherein one or more hydrogen atoms of any of the foregoing is replaced with a halogen, cyano, or amino group. R is preferably an alkyl radical and most preferably a methyl group.

$R^1$ is preferably an alkylene group of the general formula $-C_nH_{2n}-$ wherein n has a value of from about 1 to about 10, preferably from about 3 to about 6, and most preferably of about 3.

In formula (I), the sum a+b+c is preferably a number ranging from about 80 to about 500, and most preferably from about 200 to about 350; and y is preferably a number ranging from about 1 to about 20, and most preferably from about 1 to about 5.

The amine equivalent of the polysiloxane represented by formula (I) above ranges from about 0.05 to about 2.0, preferably from about 0.1 to about 1.0 and most preferably from about 0.1 to about 0.8.

The viscosity of the aminofunctional polysiloxane of this invention ranges from about 20 to about 5000, preferably from about 100 to about 3000, and most preferably from about 500 to about 2500 centipoise, at 25° C.

The novel diorganoaminoorganosiloxy-terminated polysiloxane of this invention can be prepared by any suitable method. In a particularly effective method, the siloxane is prepared by equilibrating an aminoorganoterminated polydiorganosiloxane fluid containing monofunctional siloxy, difunctional siloxy and trifunctional siloxy units, and a cyclosiloxane such as octamethylcyclotetrasiloxane. Preferably, the equilibration is effected at a temperature of 150° C. or greater in the presence of a basic equilibration catalyst such as potassium hydroxide. Those skilled in the art will readily be able to conduct such an equilibration without undue experimentation.

In this invention, the compositions for treating hair or fabric comprise (A) from about 0.1% to about 5%, preferably from about 0.5% to about 3%, and most preferably from about 1% to about 2%, by weight of the diorganoaminoorganosiloxy-terminated polysiloxanes of formula (I) and (B) from about 95% to about 99.9%, preferably from about 97% to about 99.5%, and most preferably from about 98% to about 99% by weight of a diluent selected from the group consisting of a physiologically acceptable organic solvent and an aqueous emulsion comprising water and an effective amount of an oil-in-water type surfactant.

Since the diluent serves only to dilute the silicone polymer to allow uniform application of appropriately small quantities, any diluent that is physiologically acceptable for use on the human body (when used in a hair treating composition) or an textile fabric (when used in a fabric-treating composition) may be used. For example, the silicone polymer can be dissolved in organic solvents such as alcohols, e.g., ethanol and isopropanol; and polyols, e.g., ethylene glycol and propylene glycol. Although not suitable for use on the human body, chlorinated alkanes such as 1,1,1-trichloroethane and methylene chloride can be used in compositions for treating textile fabric.

Preferably, the silicone polymer is used to treat hair or fabric in the form of an aqueous dispersion or emulsion. Aqueous emulsions of silicone polymer can be prepared by high shear mixing of the polymer in water using a suitable emulsifying surfactant as is well known in the art.

The emusifying surfactant used in the aqueous emulsion is any cationic, anionic, or nonionic organic oil-in-water type surfactant having an HLB value of from 8 to 18 inclusive. Examples of anionic surfactants include carboxylates, sulfonates, sulfates, and phosphate esters. Suitable cationic surfactants include amines, e.g., polyoxyethylene fatty amines, and quaternary salts, polyethoxylated quaternary ammonium salts. Non-ionic surfactants include polyoxyethylene derivatives of fatty alcohols, carboxylic esters, and carboxylic amides. It is preferred that the surfactant be non-ionic because non-ionic surfactants are compatible with anionic and cationic surfactants and can be used in compositions containing these surfactants without adverse effects. Specific examples of suitable non-ionic surfactants include polyoxyethylene octyl phenol containing 10 polyoxyethylene units, an alkyl ether of polyoxyethylene, an alkyl aryl ether of polyoxyethylene, trimethylnonyl polyethylene glycol ether, octyl phenoxy polyethoxy ethanol, and mixtures thereof. Most preferably, the surfactant is a mixture of approximately equal parts of trimethylnonyl polyethylene glycol ether and octyl phenoxy polyethoxy ethanol.

Microemulsions of the aminofunctional silicones in water are also suitable for use in the present invention. Microemulsions of the silicone polymers can be prepared by the method described in U.S. Pat. No. 4,620,878 (hereby incorporated by reference herein), which describes generally the preparation of emulsions of silicones containing polar substituents.

The composition of this invention is prepared by dissolving the siloxane polymer in the physiologically acceptable organic solvent or by forming an aqueous emulsion of the siloxane polymer.

Depending on the specific hair treating application, the composition of this invention may be formulated by conventional means into aerosol, pump spray, spritz, lotion, cream, gel, or mousse type compositions for easy application to hair.

In addition to the essential ingredients specified above, the composition of this invention may further comprise other ingredients which are conventional and/or beneficial. Examples of such other ingredients are thickeners and stabilizers, e.g., carboxymethyl cellulose, hydroxypropyl cellulose, and guar gum; perfumes; viscosity/foam boosters; bactericides; solvents, e.g., ethanol SDA40; organic resins, e.g., polyquaternium 11; emulsifiers, e.g., ceteareth 20, steareth 20, stearyl alcohol, and polysorbate 20; emollient oil, e.g., dimethicone and cyclomethicone; preservatives, e.g., methyl paraben methylisothiazolinone, KATHON (Registered Trade Mark) preservative, available from Rohm & Haas Company, Inc.; opacifiers; sequestering agents; pH adjusting agents, e.g., citric acid; dyes; specialty additives, such as re-fatting agents (e.g., isopropyl myristate, cetyl alcohol, propylene glycol), pearlescent agents (e.g., ethylene glycol distearate), dandruff control agents (e.g., zinc pyrithione); and conventional hair conditioning agents such as waxes, oils, stearalkonium chloride, dicetyldimonium chloride, stearamidopropyl dimethylamine, and organic quaternary compounds. The hair treating composition of the present invention may further comprise an additive that reduces static electricity build-up and fly-away. Such an additive is preferably a quaternary amine.

The hair treating composition of this invention can be applied, for example, in the form of shampoo; rinsing products to be applied after shampooing, before or after tinting or bleaching, and before or after permanent waving or straightening; products for setting or brushing; conditioning compositions; restoring compositions; and compositions for permanent-waved hair.

The hair treating composition may form a shampoo, in which case, the composition contains a cleansing surfactant in addition to the silicone polymer and the diluent. The concentration of cleansing surfactant can range from about 2 to 40 parts by weight of total composition. Cleansing surfactants selected from the group consisting of anionic surfactants, nonionic surfactants, and amphoteric surfactants are well known for use in shampoo formulations. For example, the anionic, nonionic and amphoteric surfactants useful as cleansing agents in shampoos are further described in U.S. Pat. No. 4,559,227, which is hereby incorporated by reference.

Typical cleansing surfactants include the anionic surfactants such as the sodium, ammonium, or triethanolamine salts of lauryl sulfate and lauryl ether sulfate; the nonionic surfactants such as fatty acid alkanolamides like lauric acid diethanolamide; and the amphoteric surfactants such as N-cocamidopropyl dimethyl glycine. Generally, the anionic surfactants, especially the sodium, ammonium, and triethanolamine salts of lauryl sulfate, are preferred since they provide richer, denser foams than other types of cleansing surfactants at comparable concentrations.

The hair treating composition of this invention may form a conditioning product for application to hair after shampooing. The hair is typically rinsed in running water after treatment with the conditioning composition. Conditioners facilitate combing out hair and imparts softness and suppleness to the hair. Conditioning compositions may also contain other components such as thickeners and auxiliary conditioning compounds. Auxiliary conditioning agents may be used to provide further improved conditioning benefits such as antistatic characteristics. Auxiliary conditioning agents useful in the composition of this invention include the organic cationic compounds and polymers such as stearyldimethylbenzylammonium chloride, quaternary nitrogen derivatives of cellulose ethers, and homopolymers and copolymers of dimethyldiallylammonium chloride, and other quaternary ammonium compounds which are known for use in hair conditioning formulations.

One preferred embodiment of a hair conditioning composition within the scope of this invention has the formulation:

| | |
|---|---|
| Water (distilled) | 90.35% by weight |
| Citric Acid | 0.05% by weight |
| cetearyl alcohol | 3.5% by weight |
| dicetyldimonium chloride | 1.0% by weight |
| stearamidopropyldimethylamine | 0.5% by weight |
| cyclomethicone | 1.5% by weight |
| Aminopolysiloxane Emulsion | 3.0% by weight |
| Preservative | 0.1% by weight |

*Preservative contains 95% cis-1-(3-chloroally)-3, 5, 7,-triaza-1-azoniaadamantane chloride and 4% of hexamethylenetetramine hydrochloride, percentages being based on the weight of Preservative.

In the hair-treating method of this invention, an effective amount of the composition of this invention is applied to the surface of the hair in any suitable manner such as by massaging the composition throughout the hair by hand, by dipping the hair into the composition, by brushing or combing the composition throughout the hair or by spraying.

After the composition is applied, the hair may or may not be rinsed, depending on whether the composition applied is a rinsable or non-rinsable composition.

Generally, the amount of hair treating composition that is applied is that amount which is effective to thoroughly coat the hair. The amount required will vary with the quantity and type of hair of each individual. Appropriate amounts for any individual's hair are readily determined by one or two trial applications. The length of time in which the conditioner should be left on the hair will also vary according to hair type. Generally, the conditioner is left on the hair for a period of from at least about 30 seconds to about 2 minutes.

As mentioned previously herein, the present invention is further directed to a composition and method for treating textile fabrics, wherein the aminofunctional siloxane is used. Treatment of textile fabric with the aminofunctional silicone of this invention imparts to the fabric improvements in such properties as softness, hand, wrinkle resistance, ironing ease, and soiling resistance.

The composition for treating textile fabric can contain a liquid composition consisting solely of the aminofunctional silicone of this invention. However, it is preferable that the liquid composition be prepared by dissolving or dispersing or emulsifying the aminofunctional silicone in a suitable medium such as an organic liquid or water, as described previously herein.

Emulsion compositions for practicing the textile treating method of the invention can be prepared according to known methods using any of the emulsifying agents described previously herein.

The textile-treating liquid composition of this invention may also contain non-essential components such as pigments, emulsifying agents, fire-retardant additives, plasticizers, antistatic agents and perfumes, when desired.

In the textile treating method of the present invention, the liquid composition (either the aminofunctional polysiloxane or an organic solution or aqueous emulsion thereof) is applied to at least one surface of the textile fabric in any suitable manner such as by dipping, spraying, or brushing. The applied liquid composition is then heated to a temperature of from above room temperature to less than the melting or decomposition temperature of the textile fabric. Heating may be done by any suitable method or combination of methods, but preferably is done by passing the coated textile fabric through a hot air oven. The coated fabric should be heated for an amount of time sufficient to evaporate any water that is present.

It should be understood that the method for treating textile fabric can be used to modify an end product textile or an intermediate textile. For example, it is within the intended scope of the present invention to modify a fiber or filament at any point during or after its preparation and subsequently fabricate an article such as a yarn, a fabric, or a garment from the modified fiber or filament. Alternatively, a fabric or a garment fashioned from a fiber or filament, and, subsequently, treated according to the method of the present invention.

The following examples further describe and demonstrate embodiments within the scope of the present invention. The examples are given solely for the purpose of illustration and are not to be construed as limitations of the present invention as many variations thereof are possible without departing from its spirit and scope.

Unless otherwise indicated, all parts are by weight.

EXPERIMENTAL

Example 1

Example 1 illustrates the preparation of an aminofunctional silicone within the scope of the present invention.

To a three liter round bottom flask equipped with thermometer, nitrogen blanket, condensor, water trap, agitator, and thermal controller, there was added 115 grams of $M^1D_{7.7}M^1$, i.e., bisaminopropyl (dimethyl) siloxane, 170 grams of silanol-stopped siloxane intermediate (93% dimethyl and 7% methyl), 1430 grams of octamethylcyclotetrasiloxane, and 2 grams of tetramethyl ammonium hydroxide solution. The mixture was cooked for 16 hours at 80° C. and the solids content went to 87%, indicating an equilibrated oil. The fluid was then heated to 140° C. to destroy the catalyst. After the catalyst was destroyed, the fluid was stripped at 170° C. under nitrogen sparge at a vacuum of less than 10 mm. The fluid was then filtered through Celite #545. The resulting product had a viscosity of 550 centipoise at 25° C. and a solids content of 96.6% solids.

Example 2

Example 2 illustrates the preparation of an emulsion of the aminofunctional silicone prepared in Example 1 above.

700 grams of the fluid prepared in Example 1 above were blended with 80 grams of surfactant, i.e., 90% trimethyl-4-nonlyloxypolyethyleneoxyethoxyethanol), 200 grams of water, and 0.18% of Proxel GXL biocide. The premix was stirred slowly and held at 45° C. The premix was then passed through a colloid mill with 8-10 mil gap at 25-30 psi (i.e., "pounds per square inch") pressure. The resulting translucent paste was diluted with water to yield a product having a total solids content of 36.5%.

Example 3 and Comparison Examples A and B

Three hair conditioner compositions having the formulations set forth in Table 1 below were prepared. The three compositions differed in the type of aminofunctional silicone polymer used.

The aminofunctional silicone used in the hair conditioner composition of Example 3 was a branched aminofunctional dimethylpolysiloxane containing terminal amine groups and having an amine equivalent of 0.15 milliequivalents (meq) and a viscosity of 500 centipoise at 25° C. The aminofunctional silicone used in Example 3 will sometimes be referred to herein as "Polymer G".

The aminofunctional silicone used in the hair conditioner composition of Comparison Example A was a linear aminofunctional dimethylpolysiloxane containing pendant (i.e., along the chain) amine groups and having an amine equivalent of 0.8 milliequivalents (meq) and a viscosity of 2000 centipoise at 25° C. The aminofunctional silicone used in Comparison Example A will sometimes be referred to herein as "Polymer D".

An aminofunctional silicone was not used in the hair conditioner composition of Comparison B.

TABLE 1

Formulations: Example 3 and Comparison Examples A and B

| | Weight Percent | Function |
|---|---|---|
| Part A | | |
| Ceteareth 20 | 1.0 | Emulsifier |
| Stearyl Alcohol | 2.0 | Re-fatting Agent |
| Stearamidopropyl dimethylamine | 0.8 | Conditioning Additive |
| Quaternium 18 | 1.4 | Conditioning Additive |
| Cyclomethicone | 3.0 | Wet-combing Additive |
| Part B | | |
| Water | 88.7 | |
| Part C | | |
| Silicone Emulsion | 3.0 | Conditioning and Shine Additive |
| KATHON (Registered Trademark) preservative | 0.1 | Preservative |

In Table 1 above, the silicone emulsion contains the formulation set forth in Table 2 below:

TABLE 2

Silicone Emulsion Formulation

| Ingredient | Weight Percent |
|---|---|
| Aminofunctional Silicone | 35.0 |
| Non-ionic Surfactants | 6.0 |
| Water | 58.5 |
| Preservative | 0.5 |

The hair conditioning properties of the three compositions prepared in Example 3 and Comparison Examples A and B were tested on bleached European hair tresses and compared on the basis of softness and flexibility, ease of wet and dry combing, and snarling. The rating scale ranged from 1 to 5, with 1 being worst and 5 being best. The results are shown in Table 3.

TABLE 3

Example 3 and Comparison Examples A and B: Summary of Conditioning Properties

| Property | Example 3 | Comparison Example A | Comparison Example B |
|---|---|---|---|
| Snarling | 4.0 | 3.5 | 2.0 |
| Wet Combing | 4.5 | 4.0 | 2.0 |
| Dry Combing | 4.0 | 3.5 | 2.5 |
| Softness and Flexibity | 4.0 | 4.0 | 2.5 |

The results shown in Table 3 above indicate that the hair conditioning composition containing an aminofunctional silicone polymer having terminal amine groups (Example 3) provided significant conditioning benefits as compared to the hair conditioning composition having no aminofunctional silicone (Comparison Example B). The results in the table further indicate that the hair conditioning composition containing an aminofunctional silicone having terminal amine groups provided conditioning properties which were comparable to or somewhat better than those of the hair conditioning composition containing an aminofunctional silicone having pendant amine groups (Comparison Example A).

Example 4 and Comparison Examples C and D

In Example 4 and Comparison Example C, hair conditioning compositions identical to those prepared in Example 3 and Comparison Example A, respectively, were prepared and tested for conditioning properties by means of half-head salon tests. In each comparison, a 10 member panel of females with damaged hair, i.e., permed, bleached, or frosted hair, was used. In the half-head tests, the hair of the individual panelists was washed twice with Johnson's Baby Shampoo (10 milliliters of the shampoo was used in the first washing, 6 milliliters was used in the second washing) and then parted in the middle. Ten milliliters of one of the the two conditioning compositions being compared were applied to one side of the head, and ten milliliters of the other conditioning composition were applied to the other side. The conditioner was massaged into the hair and left on for 1-2 minutes after which it was rinsed thoroughly. The hair was then evaluated for wet combing characteristics, after which the hair was dried and evaluated for dry combing characteristics.

The hair conditioning composition used in Example 4 was identical to that used in Example 3, i.e., the hair conditioning composition contained a branched aminofunctional dimethylpolysiloxane containing terminal amine groups and having an amine equivalent of 0.15 milliequivalents (meq) and a viscosity of 500 centipoise at 25° C. ("Polymer G"). The hair conditioning composition used in Comparison Example C was identical to that used in Comparison Example A, i.e., the hair conditioning composition contained a linear aminofunctional dimethylpolysiloxane having pendant (i.e., along the chain) amine groups and an amine equivalent of 0.8 milliequivalents (meq) and a viscosity of 2000 centipoise at 25° C. ("Polymer D").

The conditioning properties evaluated were ease of wet combing (detangling), ease of wet combing (subsequent), ease of dry combing, fly-away, luster, feel of hair, degree of conditioning, body, fullness, and bounce. The characteristics were evaluated by a licensed beautician and by the individual panelists. The rating scale was based on the following system:

4.0-6.0 = Acceptable 2.1-3.9 = Marginally Acceptable 1.0-2.0 = Unacceptable

The mean rating scores for Example 4 and Comparison Example C as evaluated by a licensed beautician are shown in Table 4 below and the mean rating scores as evaluated by the panelists are shown in Table 5.

TABLE 4

Example 4 and Comparison Example C:
Half-Head Testing Scores
As Provided By Licensed Beautician

| Properties | Example 4 | Comparison Example C |
|---|---|---|
| Ease of Wet Combing-Detangling | 5.4 | 5.0 |
| Ease of Wet Combing-Subsequent | 5.4 | 5.0 |
| Ease of Dry Combing | 4.8 | 4.1 |
| Fly-Away | 4.7 | 4.6 |
| Luster | 4.5 | 4.9 |
| Feel of Hair | 4.3 | 4.1 |
| Degree of Conditioning | 3.7 | 3.7 |
| Body | 3.8 | 3.9 |
| Fullness | 4.0 | 4.1 |
| Bounce | 4.1 | 4.1 |

TABLE 5

Example 4 and Comparison Example C:
Half-Head Testing Scores
As Provided By Individual Panelists

| Properties | Example 4 | Comparison Example C |
|---|---|---|
| Fly-Away | 4.3 | 4.3 |
| Luster | 4.5 | 3.6 |
| Feel of Hair | 4.8 | 4.2 |
| Degree of Conditioning | 3.6 | 3.5 |
| Body | 4.6 | 3.5 |
| Fullness | 4.2 | 3.7 |
| Bounce | 4.4 | 3.3 |

The composition containing Polymer G (Example 4) was found by the individual panelists to provide significantly better luster properties than the composition containing Polymer D (Comparison Example C). The other scoring averages were also higher for Polymer G but were not statistically significant due to a large standard deviation in the results.

Example 5 and Comparison Example D

These examples compare the conditioning properties imparted to hair by a composition identical to that used in Examples 3 and 4 (Example 5) with the conditioning properties imparted to hair by a composition identical to that used in Examples 3 and 4 except that instead of the amine-terminated silicone, a linear aminofunctional amodimethicone silicone ("Polymer A") having a viscosity of 250 centistokes at 25° C. and an amine equivalent of approximately 0.5–0.6 milliequivalent per gram is used (Comparison Example D).

The compositions prepared in Example 5 and Comparison Example D were tested for conditioning properties by means of half-head salon tests, conducted as described previously herein. The conditioning properties evaluated were ease of wet combing (detangling), ease of wet combing (subsequent), ease of dry combing, fly-away, luster, feel of hair, degree of conditioning, body, fullness, and bounce. The characteristics were evaluated by a licensed beautician and by the individual panelists in the manner indicated previously herein. The rating scale described above was also used in these examples.

The mean rating scores for Example 5 and Comparison Example D as evaluated by a licensed beautician are shown in Table 6 below and the scores as evaluated by the panelists are shown in Table 7.

TABLE 6

Example 5 and Comparison Example D:
Half-Head Testing Scores
As Provided By Licensed Beautician

| Properties | Example 5 | Comparison Example D |
|---|---|---|
| Ease of Wet Combing-Detangling | 4.5 | 4.6 |
| Ease of Wet Combing-Subsequent | 4.7 | 4.6 |
| Ease of Dry Combing | 4.5 | 3.9 |
| Fly-Away | 4.3 | 4.0 |
| Luster | 4.2 | 3.8 |
| Feel of Hair | 4.3 | 3.8 |
| Degree of Conditioning | 3.8 | 3.5 |
| Body | 3.8 | 3.8 |
| Fullness | 3.8 | 3.8 |
| Bounce | 3.9 | 3.8 |

TABLE 7

Example 5 and Comparison Example D:
Half-Head Testing Scores
As Provided By Individual Panelists

| Properties | Example 5 | Comparison Example D |
|---|---|---|
| Fly-Away | 4.6 | 4.2 |
| Luster | 4.3 | 3.7 |
| Feel of Hair | 4.1 | 3.7 |
| Degree of Conditioning | 2.8 | 2.6 |
| Body | 4.1 | 3.6 |
| Fullness | 4.0 | 3.7 |
| Bounce | 3.8 | 3.5 |

As can be seen from the scores recorded in Tables 6 and 7 above, the composition containing Polymer G (Example 5) provided properties comparable to or better than those provided by the composition containing Polymer A (Comparison Example D).

What is claimed is:

1. A composition comprising by weight:
   (A) from about 0.1% to about 5% of a diorganoaminoorganosiloxy-terminated polysiloxane composition having the general formula:

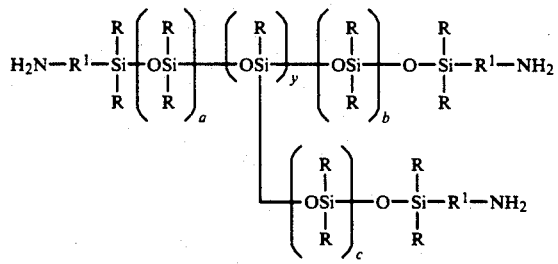

wherein each R is independently a substituted or unsubstituted hydrocarbon radical; each $R^1$ is independently a divalent alkylene, alkarylene or arylene radical; a, b, and c are numbers having values such that the sum a+b+c equals a number ranging from about 20 to about 1000; each y is a number ranging from about 1 to about 100; the amine equivalent of the polysiloxane ranges from about 0.05 to about 2.0; and the viscosity ranges from about 20 to about 5000 centipoise at 25° C.; and
   (B) from about 95% to about 99.9% of a diluent selected from the group consisting of a physiologically acceptable organic solvent and an aqueous emulsion comprising water and an effective amount of an oil-in-water type surfactant having an HLB value of from 8 to 18 inclusive.

2. The composition of claim 1, wherein component (A) is present in an amount within the range of from about 0.5% to about 3% and component (B) is present in an amount within the range of from about 97% to about 99.5%.

3. The composition of claim 2 wherein component (A) is present in an amount within the range of from about 1% to about 2% and component (B) is present in an amount within the range of from about 98% to about 99%.

4. The composition of claim 1 wherein the diluent is an aqueous emulsion comprising water and an effective amount of an oil-in-water type surfactant having an HLB value of from 8 to 18 inclusive.

5. The composition of claim 4 wherein the oil-in-water type surfactant is a cationic surfactant selected from the group consisting of polyethoxylated quaternary ammonium salts and polyoxyethylene fatty amines.

6. The composition of claim 4 wherein the oil-in-water type surfactant is a nonionic surfactant selected from the group consisting of polyoxyethylene octyl phenol containing 10 polyoxyethylene units, an alkyl ether of polyoxyethylene, an alkyl aryl ether of polyoxyethylene, trimethylnonyl polyethylene glycol ether, octyl phenoxy polyethoxy ethanol, and mixtures thereof.

7. The composition of claim 6 wherein the nonionic surfactant is a mixture of approximately equal parts of trimethylnonyl polyethylene glycol ether and octyl phenoxy polyethoxy ethanol.

8. The composition of claim 4 wherein the oil-in-water type surfactant is an anionic surfactant.

9. The composition of claim 8 wherein the anionic surfactant is selected from the group consisting essentially of carboxylates, sulfonates, sulfates, and phosphate esters.

10. The composition of claim 1 further comprising thickeners; stabilizers; perfumes; viscosity/foam boosters; bactericides; solvents; organic resins; emulsifiers; emollient oil; preservatives; opacifiers; sequestering agents; pH adjusting agents; re-fatting agents; pearlescent agents; dandruff control agents; waxes; oils; stearalkonium chloride; dicetyldimonium chloride; stearamidopropyl dimethylamine; and organic quaternary compounds.

11. A hair treating composition comprising the composition of claim 1 and further comprising a perfume.

12. A composition of claim 1 wherein the composition further comprises a cleansing surfactant and is a shampoo.

13. A composition of claim 1 wherein the composition further comprises an auxiliary conditioning agent and is a hair conditioning composition.

14. A composition of claim 1 wherein the composition further comprises a thickener and a stabilizer and is a hair styling gel.

15. A composition of claim 1 wherein the composition further comprises a solvent and is a hair spray.

16. A composition of claim 1 wherein the composition further comprises an organic resin and is a mousse.

17. A hair treating composition comprising by weight:
   (a) 90.35% of water;
   (b) 0.05% of citric acid;
   (c) 3.5% of cetearyl alcohol;
   (d) 1.0% of dicetyldimonium chloride;
   (e) 0.5% of stearamidopropyldimethylamine;
   (f) 1.5% of cyclomethicone;

(g) 3.0% of the emulsion of claim 16; and
(h) 0.1% of a preservative comprising by weight 95% cis-1-(3-chloroally)-3,5,7,-triaza-1-azoniaadamantane chloride and 4% of hexamethylenetetramine hydrochloride.

18. A method of treating hair comprising the step of contacting hair with an effective amount of the composition of claim 1.

19. A method of treating hair comprising the step of contacting hair with an effective amount of the composition of claim 17.

20. A fabric treating composition comprising the composition of claim 1 and a medium selected from the group consisting of an organic liquid or water.

21. A method for treating a textile fabric, comprising the step of contacting the surface of the textile fabric with an effective amount of the diorganoaminoorganosiloxy-terminated polysiloxane composition of claim 1.

22. A method according to claim 21 wherein the textile fabric is polyester, polyester cotton, polyester cotton, polyester rayon, cotton, rayon, or nylon.

23. A method for treating a textile fabric, comprising the step of contacting the surface of the textile fabric with an effective amount of the composition of claim 1.

24. A method according to claim 23 wherein the textile fabric is polyester, polyester cotton, polyester cotton, polyester rayon, cotton, rayon, or nylon.

* * * * *